United States Patent
Deligianni et al.

(10) Patent No.: US 10,722,729 B2
(45) Date of Patent: Jul. 28, 2020

(54) PROBE FOR LOCALIZED NEURAL OPTOGENETICS STIMULATION AND NEUROCHEMISTRY RECORDINGS

(71) Applicant: INTERNATIONAL BUSINESS MACHINES CORPORATION, Armonk, NY (US)

(72) Inventors: Hariklia Deligianni, Alpine, NJ (US); Shu-Jen Han, Yorktown Heights, NY (US); Edmund J. Sprogis, Myrtle Beach, SC (US)

(73) Assignee: International Business Machines Corporation, Armonk, NY (US)

( * ) Notice: Subject to any disclaimer, the term of this patent is extended or adjusted under 35 U.S.C. 154(b) by 330 days.

(21) Appl. No.: 15/403,651

(22) Filed: Jan. 11, 2017

(65) Prior Publication Data

US 2018/0193663 A1 Jul. 12, 2018

(51) Int. Cl.
*A61N 5/06* (2006.01)
*A61B 5/04* (2006.01)

(52) U.S. Cl.
CPC ........ *A61N 5/0622* (2013.01); *A61B 5/04001* (2013.01); *A61N 5/0601* (2013.01); *A61B 2562/0209* (2013.01); *A61N 2005/0612* (2013.01); *A61N 2005/0651* (2013.01); *A61N 2005/0652* (2013.01);
(Continued)

(58) Field of Classification Search
None
See application file for complete search history.

(56) References Cited

U.S. PATENT DOCUMENTS

2009/0210039 A1 8/2009 Boyden et al.
2011/0101394 A1* 5/2011 McKenzie .......... C23C 18/1657
257/98
(Continued)

FOREIGN PATENT DOCUMENTS

WO 2016/077412 A1 5/2016

OTHER PUBLICATIONS

Ayub et al., "High-Density Probe with Integrated Thin-Film Micro Light Emitting Diods (uLEDs) for Optogenetic Applications", 29th International Conference on Micro Electro Mechanical Systems (MEMS 2016). Jan. 24-28, 2016. pp. 379-382.
(Continued)

*Primary Examiner* — Ankit D Tejani
(74) *Attorney, Agent, or Firm* — Tutunjian & Bitetto, P.C.; Vazken Alexanian

(57) ABSTRACT

A neural probe is presented for local neural optogenetics stimulation and neurochemistry recordings. The neural probe includes a probe body, a shank extending from the probe body to a tip, a plurality of micro light-emitting diodes (LEDs) positioned across a length of a first surface of the shank for providing neuron-affecting light, a plurality of carbon devices, and a plurality of carbon electrodes positioned across a length of a second surface of the shank, the second surface in opposed relation to the first surface. The plurality of carbon electrodes can be vertically aligned carbon nanotubes or vertically aligned carbon nanofibers. The plurality of carbon electrodes can also be horizontally aligned carbon nanotubes. The plurality of micro LEDs activate neurons and the plurality of vertically aligned carbon electrodes electrochemically record neurotransmitters.

20 Claims, 14 Drawing Sheets

(52) U.S. Cl.
CPC .......... *A61N 2005/0653* (2013.01); *A61N 2005/0659* (2013.01); *A61N 2005/0663* (2013.01)

(56) References Cited

U.S. PATENT DOCUMENTS

| | | | |
|---|---|---|---|
| 2014/0142664 A1 | 5/2014 | Roukes et al. | |
| 2014/0200431 A1 | 7/2014 | Jamieson et al. | |
| 2014/0276248 A1* | 9/2014 | Hall | A61N 1/0452 601/2 |
| 2014/0329707 A1* | 11/2014 | Naughton | A61B 5/04001 506/9 |
| 2014/0356892 A1 | 12/2014 | Hoffman et al. | |
| 2015/0128413 A1 | 5/2015 | Vetter et al. | |
| 2015/0141844 A1 | 5/2015 | Viens et al. | |
| 2015/0148643 A1 | 5/2015 | Small et al. | |
| 2016/0066789 A1* | 3/2016 | Rogers | A61N 1/05 604/20 |
| 2016/0096035 A1* | 4/2016 | Lundmark | A61M 37/0015 607/92 |
| 2016/0143551 A1 | 5/2016 | Yoon et al. | |
| 2016/0218143 A1* | 7/2016 | Chaji | H01L 27/156 |

OTHER PUBLICATIONS

Chamanzar et al., "Ultracompact Optoflex Neural Probes for High-Resolution Electrophysiology and Optogenetic Stimulation", 28th IEEE International Conference on Micro Electro Mechanical Systems (MEMS). Jan. 18-22, 2015. pp. 682-685.

Fan et al., "An Implantable, Miniaturized SU-8 Optical Probe for Optogenetics-Based Deep Brain Stimulation", 36th Annual International Conference of the IEEE Engineering in Medicine and Biology Society. Aug. 26-30, 2014. pp. 450-453.

McCall et al., "Fabrication and application of flexible, multimodal light-emitting devices for wireless optogenetics", Nature Protocols. vol. 8, No. 12. Nov. 7, 2013. pp. 2413-2428.

Park et al., "Graphene-based carbon-layered electrode array technology for neural imaging and optogenetic applications", Nature Communications. Article No. 5258. Oct. 20, 2014. pp. 1-11.

Rand et al., "A carbon nanofiber based biosensor for simultaneous detection of dopamine and serotonin in the presence of ascorbic acid", Supplentary Data. Biosensors and Bioelectronics. vol. 42. Apr. 15, 2013. pp. 1-5.

Scharf et al., "Depth-specific optogenetic control in vivo with a scalable, high-density uLED neural probe", Scientific Reports. Article No. 28381. Jun. 23, 2016. pp. 1-10.

Schwaerzle et al., "High-Resolution Neural Depth Probe with Integrated 460 NM Light Emitting Diode for Optogenetic Applications", 18th International Conference on Solid-State Sensors, Actuators and Microsystems (Transducers) Jun. 21-25, 2015. pp. 1774-1777.

\* cited by examiner

PROBE FOR LOCALIZED NEURAL OPTOGENETICS STIMULATION AND NEUROCHEMISTRY RECORDINGS

BACKGROUND

Technical Field

The present invention relates generally to optogenetics, and more specifically, to a neural probe for performing localized neural optogenetics stimulation and neurochemistry recordings at the same time.

Description of the Related Art

Electrical neural stimulation and modulation is important in many basic science applications, as well as many clinical applications. Some of the approved electrical stimulators include artificial cardiac pacemakers, cochlear implants, and deep brain stimulation electrodes. A challenge with this technology is achieving a highly localized stimulated area (i.e., a small population of neurons).

Massively-parallel access to the activity of large populations of individual neurons with high spatial and temporal resolution has been a long-sought goal in neuroscience. With advances in microelectromechanical systems (MEMS) and microelectronics, there has been progress toward this goal as planar fabrication processes have been applied to realize chronic extracellular microelectrode arrays. Many reported neural probes use electrical signals to stimulate neurons. However, such electrical stimulation is not necessarily specific to a neural circuit and can damage neurons as far as 500 microns away from the stimulation site.

SUMMARY

In accordance with an embodiment, a method is provided for stimulating excitable tissue. The method includes introducing a neural probe into target excitable tissue, the neural probe including a probe body, a shank extending from the probe body to a tip, a plurality of micro light-emitting diodes positioned across a length of a first surface of the shank for providing neuron-affecting light, carbon nanotube circuitry, and a plurality of carbon electrode sensors positioned across a length of a second surface of the shank, the second surface in opposed relation to the first surface. The method further includes activating neurons via the plurality of micro LEDs and electrochemically recording neurotransmitters via the plurality of carbon electrode sensors.

In accordance with another embodiment, a neural probe is provided. The neural probe includes a probe body, a shank extending from the probe body to a tip, a plurality of micro light-emitting diodes (LEDs) positioned across a length of a first surface of the shank for providing neuron-affecting light, a plurality of carbon devices, and a plurality of vertically aligned carbon electrodes positioned across a length of a second surface of the shank, the second surface in opposed relation to the first surface. The plurality of micro LEDs activate neurons and the plurality of vertically aligned carbon electrodes electrochemically record neurotransmitters.

In accordance with another embodiment, a neural probe is provided. The neural probe includes a probe body, a shank extending from the probe body to a tip, a plurality of micro light-emitting diodes positioned across a length of a first surface of the shank for providing neuron-affecting light, a plurality of carbon devices, and a plurality of horizontally aligned carbon electrodes positioned across a length of a second surface of the shank, the second surface in opposed relation to the first surface. The plurality of micro LEDs activate neurons and the plurality of horizontally aligned carbon electrodes electrochemically record neurotransmitters.

It should be noted that the exemplary embodiments are described with reference to different subject-matters. In particular, some embodiments are described with reference to method type claims whereas other embodiments have been described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be described within this document.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The invention will provide details in the following description of preferred embodiments with reference to the following figures wherein.

Throughout the drawings, same or similar reference numerals represent the same or similar elements.

DETAILED DESCRIPTION

Figure 1:
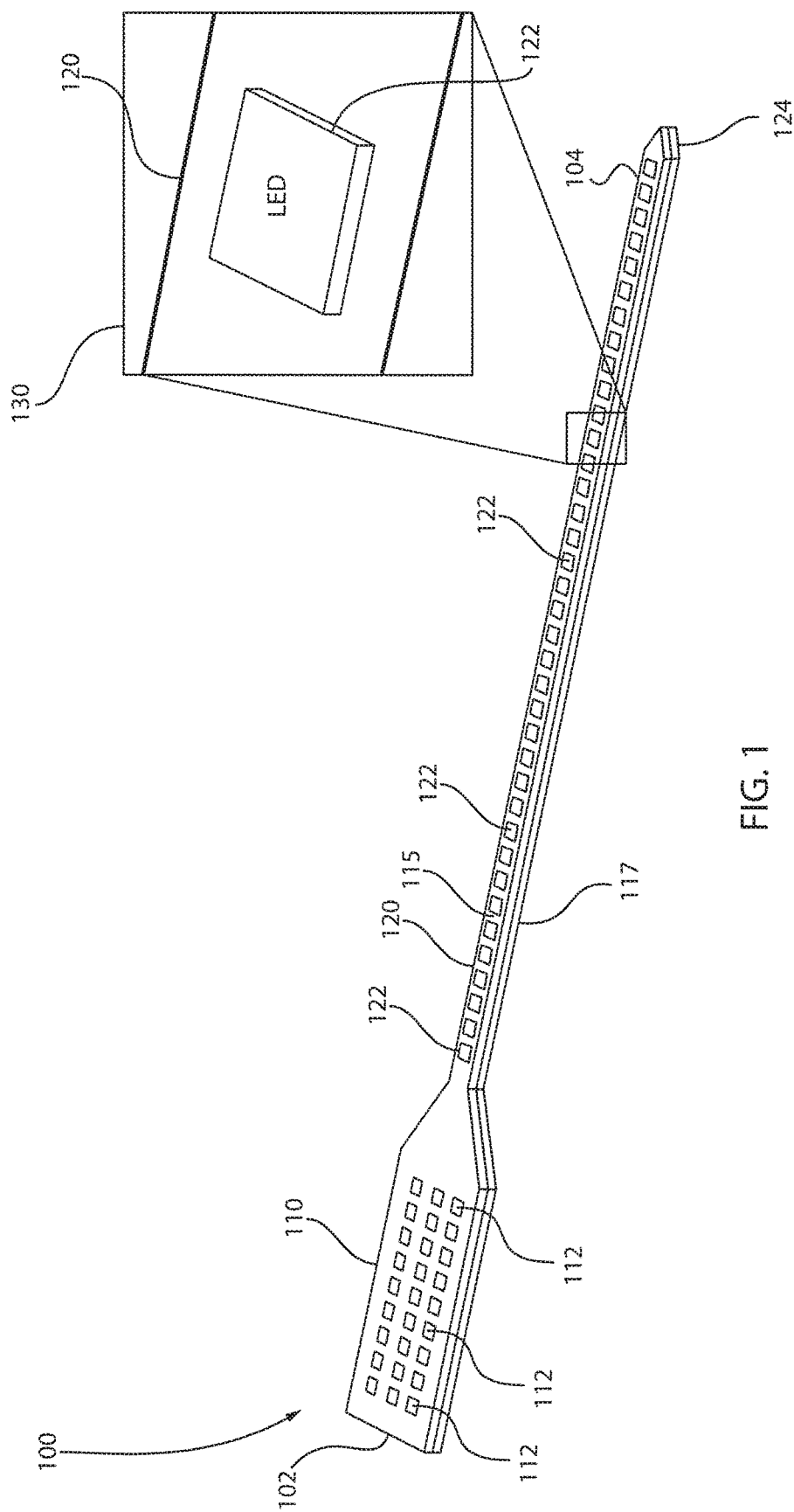
FIG. 1 is a perspective view of a neural probe with LED stimulation, carbon nano-tube circuitry, and carbon electrode sensors, in accordance with an embodiment of the present invention.

Embodiments of the present invention relate generally to a method of stimulating excitable tissue. The method includes introducing a neural probe into target excitable tissue, the neural probe having a probe body, a shank extending from the probe body to a tip, a plurality of micro light-emitting diodes (µLEDs) positioned across a length of a first surface of the shank for providing neuron-affecting light, and a plurality of carbon electrode sensors positioned across a length of a second surface of the shank, the second surface in opposed relation to the first surface. The method further includes activating neurons via the plurality of µLEDs and electrochemically recording neurotransmitters via the plurality of carbon electrode sensors at the same time (simultaneously or sequentially).

Moreover, embodiments of the present invention relate generally to a neural probe. The neural probe includes a probe body, a shank extending from the probe body to a tip, a plurality of micro light-emitting diodes (µLEDs) positioned across a length of a first surface of the shank for providing neuron-affecting light, and a plurality of carbon electrode sensors positioned across a length of a second surface of the shank, the second surface in opposed relation to the first surface. The plurality of µLEDs activate neurons and the plurality of carbon electrode sensors electrochemically record neurotransmitters at the same time (simultaneously or sequentially).

In one or more embodiments, the LED device and the sensor are built by at least defining an LED die on a blanket film GaN wafer, transferring the LED die to a handler and removing a sapphire substrate, building a vertically aligned carbon CNT or CNF layer on a Si wafer, bonding it to a handler, building carbon circuitry and wiring, transferring the LED die to the carbon device wafer by bonding, building an LED wire level, and performing passivation and encapsulation.

In one or more embodiments, the invention teaches a fully flexible neural probe which can both activate neurons using the blue µLEDs, but it can also record neural electrical activity and the resulting neurochemistry in the extracellular or intracellular neuronal space. More specifically, the flexible probe can activate and record neural activity but it can electrochemically record neurotransmitters such as dopamine, serotonin, adenosine, DOPAC and other neurochemicals all at the same time or sequentially. The electrodes can be carbon electrodes and are excellent catalysts for the adsorption and electro-oxidation of neurochemicals. In one embodiment, the carbon electrode sensors can be vertically aligned carbon nanotubes (CNT) or vertically aligned carbon nanofibers (CNF) (e.g., FIGS. 6-15). In another embodiment, the carbon electrode sensors can be horizontally aligned carbon nanotubes (CNT) (e.g., FIGS. 16-22). The carbon electrodes are electrochemically active materials. The invention does not propose a neurotransmitter delivery system. Instead, the present invention proposes an activation system using µLEDs and a recording system of the resulting neurochemistry, where both features are executed simultaneously or sequentially via the neural probe.

In one or more embodiments, the neural probe allows for stimulation at the electrode-tissue interface and for recording the neural response and the resulting neurochemical release of dopamine, serotonin, adenosine, DOPAC, glutamate at the same time. The neural probe can be a flexible neural probe structure with optogenetic µLEDS, carbon electronics, and carbon electrodes. Stated differently, the neural probe can be a fully flexible carbon-based implantable electrode probe for multi-functional dopamine and pH sensing with local optogenetic neural activation.

As used herein, a light-emitting diode (LED) is a semiconductor device that emits light when an electric current is passed through it. Light is produced when the particles that carry the current (known as electrons and holes) combine together within the semiconductor material.

Since light is generated within the solid semiconductor material, LEDs are described as solid-state devices. The term solid-state lighting, which also encompasses organic LEDs (OLEDs), distinguishes this lighting technology from other sources that use heated filaments (incandescent and tungsten halogen lamps) or gas discharge (fluorescent lamps).

Inside the semiconductor material of the LED, the electrons and holes are contained within energy bands. The separation of the bands (i.e., the bandgap) determines the energy of the photons (light particles) that are emitted by the LED.

The photon energy determines the wavelength of the emitted light, and hence its color. Different semiconductor materials with different bandgaps produce different colors of light. The precise wavelength (color) can be tuned by altering the composition of the light-emitting, or active, region.

LEDs are comprised of compound semiconductor materials, which are made up of elements from group III and group V of the periodic table (these are known as III-V materials). Examples of III-V materials commonly used to make LEDs are gallium arsenide (GaAs), gallium phosphide (GaP) and gallium nitride (GaN).

The main semiconductor materials used in LEDs are:

Indium gallium nitride (InGaN): blue, green and ultraviolet high-brightness LEDs.

Aluminum gallium indium phosphide (AlGaInP): yellow, orange and red high-brightness LEDs.

Aluminum gallium arsenide (AlGaAs): red and infrared LEDs.

Gallium phosphide (GaP): yellow and green LEDs.

Different color LEDs can activate/deactivate different neural circuits and influence the resulting release of neurochemicals.

As used herein, "semiconductor device" refers to an intrinsic semiconductor material that has been doped, that is, into which a doping agent has been introduced, giving it different electrical properties than the intrinsic semiconductor. Doping involves adding dopant atoms to an intrinsic semiconductor, which changes the electron and hole carrier concentrations of the intrinsic semiconductor at thermal equilibrium. Dominant carrier concentration in an extrinsic semiconductor determines the conductivity type of the semiconductor.

A "gate structure" means a structure used to control output current (i.e., flow of carriers in the channel) of a semiconducting device through electrical or magnetic fields.

As used herein, the term "drain" means a doped region in the semiconductor device located at the end of the channel, in which carriers are flowing out of the transistor through the drain.

As used herein, the term "source" is a doped region in the semiconductor device, in which majority carriers are flowing into the channel.

As used herein, the term "raised" in combination with source and/or drain denotes that the source and/or drain region is formed over a semiconductor material layer that is present on an upper surface of the substrate on which the gate dielectric is present.

The term "direct contact" or "directly on" means that a first element, such as a first structure, and a second element, such as a second structure, are connected without any intermediary conducting, insulating or semiconductor layers at the interface of the two elements.

The terms "overlying", "atop", "positioned on" or "positioned atop" means that a first element, such as a first structure, is present on a second element, such as a second structure, wherein intervening elements, such as an interface structure can be present between the first element and the second element.

The term "electrically connected" means either directly electrically connected, or indirectly electrically connected, such that intervening elements are present; in an indirect electrical connection, the intervening elements can include inductors and/or transformers.

As used herein, the terms "insulating" and "dielectric" denote a material having a room temperature conductivity of less than about $10^{-10}$ $(\Omega\text{-m})^{-1}$.

As used herein, "p-type" refers to the addition of impurities to an intrinsic semiconductor that creates deficiencies of valence electrons. In a silicon-containing substrate, examples of n-type dopants, i.e., impurities, include but are not limited to: boron, aluminum, gallium and indium.

As used herein, "n-type" refers to the addition of impurities that contributes free electrons to an intrinsic semiconductor. In a silicon containing substrate examples of n-type dopants, i.e., impurities, include but are not limited to antimony, arsenic and phosphorous.

The term "conformal" denotes a layer having a thickness that does not deviate from greater than or less than 30% of an average value for the thickness of the layer.

RIE is a form of plasma etching in which, during etching, the surface to be etched is placed on the RF powered electrode. Moreover, during RIE the surface to be etched takes on a potential that accelerates the etching species extracted from plasma toward the surface, in which the chemical etching reaction is taking place in the direction normal to the surface. Other examples of anisotropic etching that can be used include ion beam etching, plasma etching or laser ablation.

It is to be understood that the present invention will be described in terms of a given illustrative architecture; however, other architectures, structures, substrate materials and process features and steps/blocks can be varied within the scope of the present invention. It should be noted that certain features cannot be shown in all figures for the sake of clarity. This is not intended to be interpreted as a limitation of any particular embodiment, or illustration, or scope of the claims.

FIG. 1 is a perspective view of a neural probe with LED stimulation including carbon electrode sensors, in accordance with one embodiment of the present invention.

The exemplary neural probe 100 includes a probe body 110, a shank 120 extending from the probe body 110 to a tip 124. The neural probe 100 includes a proximal end 102 and a distal end 104. The neural probe 100 can be an implantable probe. The probe body 110 includes a plurality of contacts 112. The shank 120 includes a first surface 115 and a second surface 117. The first surface 115 includes a plurality of light emitting diodes (LEDs) 122 extending across a length of the shank 120. The plurality of LEDs 122 can emit neuron-affecting light at the tip 124. An example LED of the plurality of LEDs 122 is shown in expanded or enhanced view 130. Each LED of the plurality of LEDs can be about 50 µm×50 µm. Of course, one skilled in the art can contemplate other manufacturing dimensions for each of the plurality of LEDs 122.

The second surface 117 includes a plurality of sensors. The sensors can be, e.g., carbon electrode sensors. The carbon electrode sensors can be, e.g., vertically aligned carbon nanotubes (CNT) or vertically aligned carbon nanofibers (CNF). In one example, the carbon electrode sensors are integrated with the plurality of LEDs 122. Stated differently, a carbon electrode sensor forms one unitary piece or component with an LED of the plurality of LEDs 122. The carbon electrode sensors are better illustrated in FIG. 10 described below.

Probe body 110 generally serves as the portion of the probe 100 from which shank 120 extends and where various probe electrical connections are located. In this embodiment, probe body 110 and the shank 120 are integral, i.e., formed together as one unitary piece. Of course, one skilled in the art can contemplate the probe body 110 and the shank 120 to be detachably connected to each other. In other words, the probe body 110 and the shank 120 can be interchangeable. Therefore, the probe body 110 can be interchanged to interface with a plurality of different types of shanks 120.

In one embodiment, the shank 120 can extend from about 1-7 mm, preferably about 5 mm, in length from the probe body 110. The shank 120 has a width transverse to the length ranging from 50-150 µm, and a thickness from about 10-20 µm. Of course, these are only exemplary ranges, and several factors can be considered when selecting the dimensions of the shank 120, such as strength, desired depth of probing, and the number of LEDs 122 desired, to name a few.

The plurality of LEDs 122 can be, e.g., gallium nitride (GaN) LEDs or a plurality of other color LEDs. To fabricate high performance GaN based devices, GaN patterning (i.e., etching) techniques are important. Variations in the quality of the as-grown GaN, coupled with the high bond energies associated with "III-nitride" materials, present unique challenges for etching processes. Similar to etching other semiconductor materials, plasma based dry etch and chemical based wet etch are the two major etch techniques for GaN patterning. Laser patterning GaN film is also capable of achieving unique structures when combined with proper wet etching techniques to remove the ablated material and the thermal decomposition.

Typical etching gases for GaN plasma dry etch are $Cl_2$/Ar. Argon (or helium) is added to stabilize the plasma or for cooling purposes. Argon addition causes inert ion bombardment of the surface, which results in enhanced anisotropic etching, while the chlorine-based plasma produces (volatile) chemical byproducts such as $GaCl_3$. The dry etch process can achieve a highly anisotropic etch with a high etching rate and has a smooth surface morphology. Using $Cl_2$-based plasma to etch GaN is desirable because chlorine-based gas chemistry is widely used in the processing of semiconductor devices.

Moreover, the neuron-affecting light can be used to stimulate or silence individual or groups of neurons. Such light can include visible and/or non-visible light. Stimulation or silencing of multiple sites is made possible by certain variations of the described probe, as well as stimulation or silencing by more than one wavelength of light either simultaneously or sequentially. Although the following description at times refers to light stimulation of neurons and sites, without specifically mentioning the use of light to silence neurons, it will be appreciated by those skilled in the art that the light can be used for either or both purposes, depending on such things as the wavelength and intensity of the emitted light.

Figure 2:
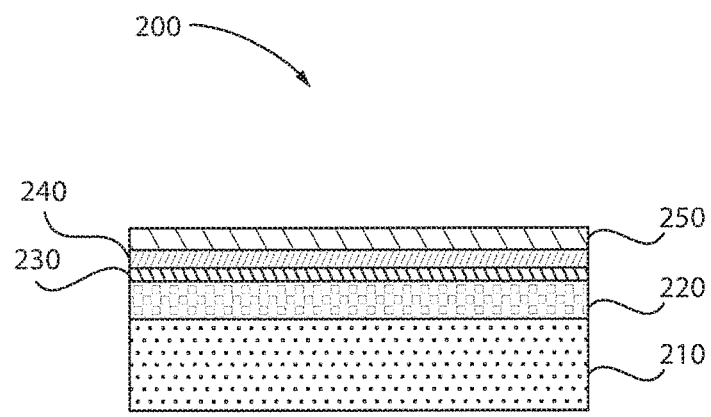
FIG. 2 is a cross-sectional view of an LED die on a blanket film gallium nitride (GaN) wafer, in accordance with an embodiment of the present invention.

FIG. 2 is a cross-sectional view of an LED die on a blanket film gallium nitride (GaN) wafer, in accordance with an embodiment of the present invention.

Gallium nitride (GaN) buffer layers are formed on a sapphire substrate 210 to form structure 200. The sapphire substrate 210 can be formed of, e.g., $Al_2O_3$ (aluminum oxide). The GaN buffer layers include a first layer 220, a second layer 230, a third layer 240, and a fourth layer 250. The first layer 220 can be, e.g., n-type GaN. The second layer 230 can be, e.g., GaInN. The third layer 240 can be, e.g., p-type GaN. The fourth layer 250 can be, e.g., a p-metal.

The p-type GaN layer 240 is in a contrast to the n-type GaN layer 220. Namely, electrons are drifted by an external voltage in the n-type GaN layer 220, while holes are drifted by the external voltage in the p-type GaN layer 240. Therefore, the holes and the electrons are mutually recombined in the layer 250, thereby emitting light. The p-type GaN layer 240 can have a thickness of about 0.2 µm. The n-type GaN layer 220 can have a thickness of about 2.5 µm. The GaInN layer 230 can have a thickness of about 0.2 µm.

GaN is a material widely used in the construction of blue, violet, and white light emitting diodes, blue laser diodes, ultraviolet detectors, and high power microwave transistor devices. GaN device technology is based on single crystal material grown at temperatures generally above 950° C. directly on sapphire or silicon carbide substrates. The growing processes are typically metal organic chemical vapor deposition (MOCVD) or molecular beam epitaxy (MBE) techniques. These processes are normally run under conditions which are as near as possible to stoichiometry. In order to form a Group III-based element in a form of a thin film on the sapphire substrate 210 as described above, a metal organic chemical vapor deposition (MOCVD) is generally used. At this time, the thin film layer is formed under a constant growth pressure.

The term "substantially" single-crystal is used in describing the GaN layers to take account of the fact that semiconductor materials normally contain at least some internal or surface defects either inherently or purposely added, such as lattice defects or a few grain boundaries. The term "substantially" also reflects the fact that certain dopants can distort or otherwise affect the crystal structure of the semiconductor material.

Substrate 210 can have a large-surface orientation between ten degrees and 0.2 degree (or less) of (0 0 0 1), (0 0 0 −1), {1 −1 0 0}, {1 1 −2 0}, {1 −1 0.+−.1}, {1 −1 0.+−.2}, {1 −1 0.+−.3}, {2 0 −2.+−.1}, or {1 1 −2.+−.2}. In one embodiment, the substrate 210 has a semipolar large-surface orientation, designated by (hkil) Bravais-Miller indices, where i=−(h+k), l is nonzero and at least one of h and k are nonzero. The substrate 210 can have a dislocation density below $10^4$ $cm^2$ and an optical absorption coefficient below 100 $cm^{10}-1$ at wavelengths between about 465 nm and about 700 nm. The nitride base crystal has an optical absorption coefficient below 100 $cm^{-1}$ at wavelengths between about 700 nm and about 6667 nm. The surface of substrate 210 can have a dislocation density below $10^5$ $cm^{-2}$ and is substantially free of low-angle grain boundaries, or tilt boundaries, over a length scale of at least 3 millimeters. The substrate 210 can be doped with any suitable n-type dopants from group VI and group IV atoms, e.g., sulfur, selenium, tellurium, silicon, germanium.

The substrate 210 can be formed from a material that can withstand the aforementioned temperature at which the GaN layers are grown, e.g., about 750° C. or higher, more particularly about 100° C. or higher, and the CTE of the substrate 210 should be close to that of GaN to avoid cracking of the GaN based layers during thermal cycling. By way of example, the substrate 210 can be formed from a material selected from the group consisting of: glass, glass-ceramic, and transparent ceramics including aluminum oxynitride, magnesium aluminate spinel, yttrium aluminate garnet, polycrystalline alumina, and sapphire.

The substrate 210 can have a thickness in the range of about 0.1 mm to about 10 mm, such as in the range of about 0.5 mm to about 3 mm. For some applications, substrates 210 having a thickness greater than or equal to about 1 micron are desirable, e.g., to avoid parasitic capacitive effects which arise when some semiconductor configurations operate at high frequencies. In one example, the substrate 210 has a thickness of 430 μm.

The GaN layers 220, 230, 240 are grown or deposited on the sapphire substrate 210. This growth process can be achieved by using one or more of the following processes: organo-metallic vapor phase epitaxy, metal organic chemical vapor deposition, molecular beam epitaxy, and hydride vapor phase epitaxy. These growth processes can be carried out at an elevated temperature, such as about 750° C. or higher, and more particularly, about 1000° C. or higher. Pulsed laser deposition can also be employed to deposit the GaN layers 220, 230, 240 on the sapphire substrate 210. Pulsed laser deposition can be performed at much lower temperatures, such as from about room temperature (e.g., about 25° C.) to about 600-700° C. and it can be possible to obtain good quality GaN even at the substantially lower temperatures.

Figure 3:
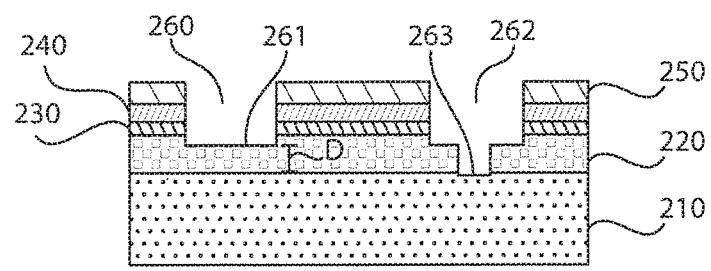
FIG. 3 is a cross-sectional view of the structure of FIG. 2 where the GaN layers are selectivity etched, in accordance with an embodiment of the present invention.

FIG. 3 is a cross-sectional view of the structure of FIG. 2 where the GaN layers are selectivity etched, in accordance with an embodiment of the present invention.

The GaN layers 220, 230, 240, 250 are selectively etched to form a first gap or recess or cavity 260 and a second gap or recess or cavity 262. The first recess 260 extends to a top surface 261 of the n-type GaN layer 220. The top surface 261 of the layer 220 is a distance "D" from the sapphire substrate 210. The second recess 262 extends up to a top surface 263 of the sapphire substrate 210. Therefore, a portion of the sapphire substrate 210 is exposed after selective etching is performed.

As used herein, the term "selective" in reference to a material removal process denotes that the rate of material removal for a first material is greater than the rate of removal for at least another material of the structure to which the material removal process is being applied. For example, in one embodiment, a selective etch can include an etch chemistry that removes a first material selectively to a second material by a ratio of 10:1 or greater, e.g., 100:1 or greater, or 1000:1 or greater.

Figure 4:
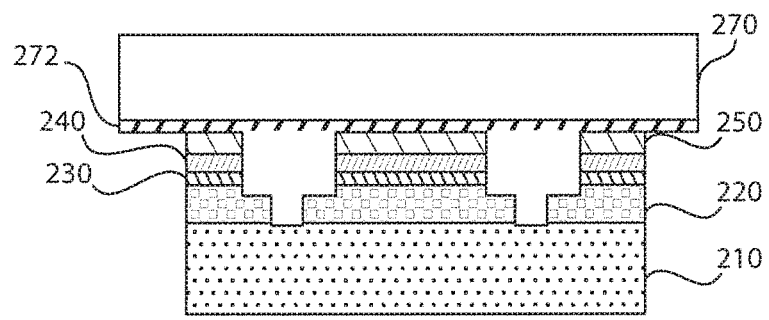
FIG. 4 is a cross-sectional view of the structure of FIG. 3 where the structure is transferred to a handler, in accordance with an embodiment of the present invention.

FIG. 4 is a cross-sectional view of the structure of FIG. 3 where the structure is transferred to a handler, in accordance with an embodiment of the present invention.

The structure of FIG. 3 is transferred to a first handler 270. The first handler 270 can be, e.g., a glass handler. A release layer 272 can be applied to the first handler 270.

The release layer 272 can be transparent so that the underlying circuitry of the silicon device wafer can be optically inspected prior to debonding. Debonding can be performed by ablating the release layer 272 using a laser. The laser used can be an ultraviolet (UV) laser, for example, a 355 nm laser. This wavelength is particularly attractive due to the availability of robust and relatively inexpensive diode-pumped solid-state (DPSS) lasers. In one example, the release layer 272 can be an ultraviolet (UV) ablation layer and it can be applied to the handling wafer, which can be glass handler 270. The UV ablation layer can then be cured.

An exemplary glass preparation process can begin with the UV ablation material being applied e.g., by spin coating onto the glass handler 270. The glass handler 270 with UV ablation material spin-coated thereon can then be soft-baked to remove any solvent. Spin coating parameters can depend on the viscosity of the UV ablation layer, but can fall in the range from approximately 500 rpm to approximately 3000 rpm. The soft-bake can fall in the range from approximately 80° C. to approximately 120° C. The temperature of the final cure can fall in the range from 200° C. to 400° C. Higher cure temperatures can be more effective at ensuring thermal stability of the UV ablation layer during standard complementary metal oxide semiconductor (CMOS) back end of line (BEOL) processing which can take place between 350° C. and 400° C. For strongly UV-absorbing or UV-sensitive materials, very thin final layers on the order of approximately 1000 Å to approximately 2000 Å thick can be sufficient to act as release layers. One such material is Shin Etsu ODL 38 which can be spin applied to glass and cured in a nitrogen environment at 350° C. for approximately 1 hour to produce a film on the order of 1000 Å thick. Such a film can be optically transparent throughout the visible spectrum, but strongly sensitive to decomposition in the UV wavelength range below ~360 nm, and can be fully and cleanly ablated using common UV laser sources such as an excimer laser operating at 308 nm (e.g., XeCl) or 351 nm (e.g., XeF) or a diode-pumped tripled YAG laser operating at 355 nm.

Laser debonding to release the glass handler 270 at the ablation layer interface can be performed using any one of a number of UV laser sources including excimer lasers operating at 308 nm (e.g., XeCl) or 351 nm (e.g., XeF), as well as diode-pumped (tripled) YAG laser operating at 355 nm or diode-pumped (quadrupled) YAG laser operating at 266 nm. Excimer lasers can be more expensive, can require more maintenance/support systems (e.g., toxic gas containment) and can have generally have very large output powers at low repetition rates (e.g., hundreds of Watts output at several hundred Hz repetition). UV ablation thresholds in the materials specified here can require 100-150 milliJoules per square cm (mJ/sq·cm) to effect release. Due to their large output powers, excimer lasers can supply this energy in a relatively large area beam having dimensions on the order of tens of mm² area (e.g. 0.5 mm×50 mm line beam shape). Due to their large output power and relatively low repetition rate, a laser debonding tool which employs an excimer laser can consist of a movable x-y stage with a fixed beam. Stage movement can be on the order of 10 to 50 mm per second. The wafer pair to be debonded can be placed on the stage, and scanned back and forth until the entire surface had been irradiated.

An alternative laser debonding system can be created using a less expensive, more robust and lower power solid-state pumped tripled YAG laser at 355 nm by rapidly scanning a small spot beam across the wafer surface. The 355 nm wavelength laser can compare favorably to the quadrupled YAG laser at 266 nm for two reasons: 1) Output powers at 355 nm are typically 2 to 3 times larger than at 266 nm for the same sized diode laser pump power, and 2) many common handler wafer glasses (e.g. Schott Borofloat 33) are ~90% or more transmissive at 355 nm but only ~15% transmissive at 266 nm. Since 80% of the power is absorbed in the glass at 266 nm, starting laser powers can be ~6× higher to achieve the same ablation fluence at the release interface, and there is risk of thermal shock in the glass handler itself.

Figure 5:
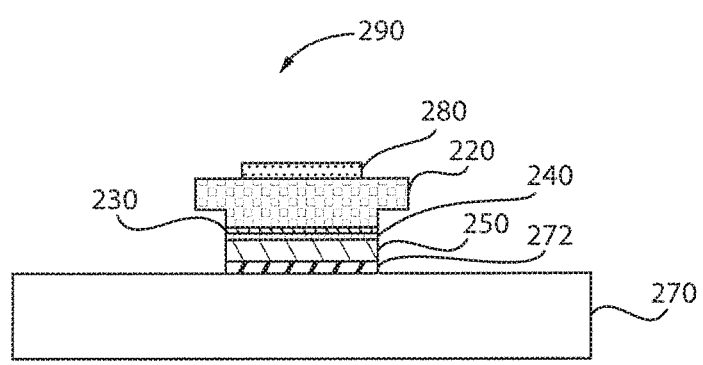
FIG. 5 is a cross-sectional view of the semiconductor device of FIG. 4 where a sapphire substrate is removed and a first bondpad is formed over a GaN layer, in accordance with an embodiment of the present invention.

FIG. 5 is a cross-sectional view of the semiconductor device of FIG. 4 where a sapphire substrate is removed and a first bondpad is formed over a GaN layer, in accordance with an embodiment of the present invention.

The sapphire substrate 210 (FIG. 4) is released or removed and a first bondpad 280 is formed on the GaN layer 220. The structure is also flipped. The structure of FIG. 5 is referred to as LED structure 290.

In various embodiments, the materials and layers can be deposited by physical vapor deposition (PVD), chemical vapor deposition (CVD), atomic layer deposition (ALD), molecular beam epitaxy (MBE), or any of the various modifications thereof, for example plasma-enhanced chemical vapor deposition (PECVD), metal-organic chemical vapor deposition (MOCVD), low pressure chemical vapor deposition (LPCVD), electron-beam physical vapor deposition (EB-PVD), and plasma-enhanced atomic layer deposition (PE-ALD). The depositions can be epitaxial processes, and the deposited material can be crystalline. In various embodiments, formation of a layer can be by one or more deposition processes, where, for example, a conformal layer can be formed by a first process (e.g., ALD, PE-ALD, etc.) and a fill can be formed by a second process (e.g., CVD, electrodeposition, PVD, etc.).

Figure 6:
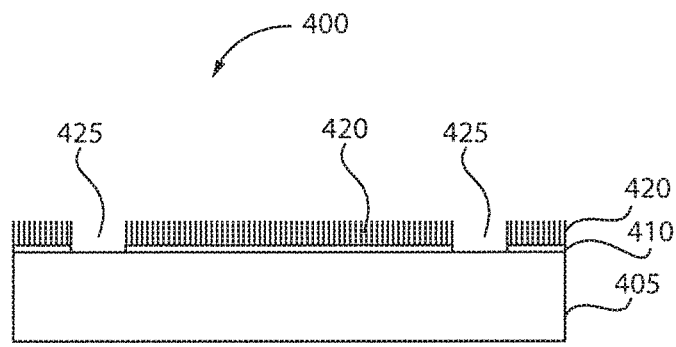
FIG. 6 is a cross-sectional view of a carbon electrode sensor structure, in accordance with an embodiment of the present invention.

FIG. 6 is a cross-sectional view of a carbon electrode sensor structure, in accordance with an embodiment of the present invention.

After forming the LED structure 290, as described above with reference to FIGS. 2-5, the sensor portion is now formed with reference to FIGS. 6-10. The LED structure 290 will be combined with the sensor portion to form the final structure (FIG. 11).

There are two types of carbon electrode sensors that can be used in the structures of FIGS. 6-15. The first type is a vertically aligned carbon nanotube (CNT) and the second type is a vertically aligned carbon nanofiber (CNF).

In a first embodiment, a carbon electrode sensor structure 400 includes a titanium (Ti) or nickel (Ni) layer 410 that is formed over the substrate 405. The substrate 405 can be, e.g., a Si substrate. Segmentation channels 425 are formed such that portions of the substrate 405 are exposed. A vertically aligned CNT or CNF layer 420 is grown over portions of the layers 410 (Ti or Ni). If Ti is used, the Ti layer 410 can have a thickness of about 200 nm. If Ni is used, the Ni layer 410 can have a thickness of about 20 nm. One skilled in the art can contemplate using other types of materials, such as, but not limited to TiN or $Ni_{45}Fe_{55}$. If TiN is used, the TiN layer 410 can have a thickness of about 200 nm. If $Ni_{45}Fe_{55}$ is used, the $Ni_{45}Fe_{55}$ layer 410 can have a thickness of about 20 nm.

In a second embodiment, a carbon electrode sensor structure 400 includes a titanium (Ti) or gold (Au) layer 410 that is formed over the substrate 405. In this example embodiment, a vertically aligned CNF layer 420 is grown. After deposition of the layer 420, a negative photoresist (not shown) is applied thereto via, e.g., spinning. The negative photoresist can be, e.g., SU-8. Negative refers to a photoresist whereby the parts exposed to UV become crosslinked, while the remainder of the film remains soluble and can be washed away during development. Subsequently, segmentation channels are formed and polystyrene beads are applied on the photoresist. The beads can be, e.g., 1 μm in thickness. Next, a plasma etch can take place, as well as ultrasonification to remove the beads. The CNF layer 420 is then pyrolyzed. Pyrolization can be performed at, e.g., 900° C.

If Ti is used, the Ti layer 410 can have a thickness of about 200 nm. If Au is used, the Au layer 410 can have a thickness of about 20 nm. The photoresist can have a thickness of about 5 μm. One skilled in the art can contemplate using other types of materials suitable for intended applications.

In one or more embodiments, the substrate 405 can be a semiconductor or an insulator with an active surface semiconductor layer. The substrate 405 can be crystalline, semi-crystalline, microcrystalline, or amorphous. The substrate 405 can be essentially (i.e., except for contaminants) a single element (e.g., silicon), primarily (i.e., with doping) of a single element, for example, silicon (Si) or germanium (Ge), or the substrate 405 can include a compound, for example, $Al_2O_3$, $SiO_2$, GaAs, SiC, or SiGe. The substrate 405 can also have multiple material layers, for example, a semiconductor-on-insulator substrate (SeOI), a silicon-on-insulator substrate (SOI), germanium-on-insulator substrate (GeOI), or silicon-germanium-on-insulator substrate (SGOI). The substrate 405 can also have other layers forming the substrate 405, including high-k oxides and/or nitrides. In one or more embodiments, the substrate 405 can be a silicon wafer. In an embodiment, the substrate 405 is a single crystal silicon wafer.

Figure 7:
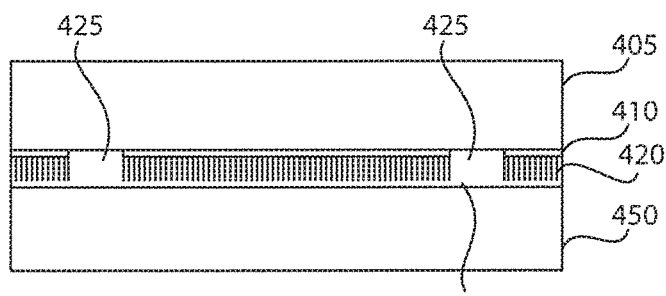
FIG. 7 is a cross-sectional view of the sensor of FIG. 6 where a release layer is applied over the CNT or CNF layer of the carbon electrode sensor, in accordance with an embodiment of the present invention.

FIG. 7 is a cross-sectional view of the sensor of FIG. 6 where a release layer is applied over the CNT or CNF layer, in accordance with an embodiment of the present invention.

A polydimethylsiloxane (PDMS) layer 440 is deposited over the CNT or CNF layer 420 and a handler 450 is placed over the PDMS layer 440. PDMS can be used as the transfer medium. PDMS has two very desirable properties that makes PDMS a good medium for transferring a resist layer. First, PDMS has a very low surface energy that facilitates resist transfer. Second, PDMS can be molded from liquid to any shape and size. In addition, PDMS is re-usable. Spin coating is a preferred method for forming the PDMS layer 440 of the wafer. An alternative method to spin coating is molding PDMS material on a large sheet and the sheet is then cut to a required size. The molded PDMS layer can be made sufficiently stiff so that the resist layer can be spun coated directly onto the molded PDMS layer without the use of the wafer.

Figure 8:
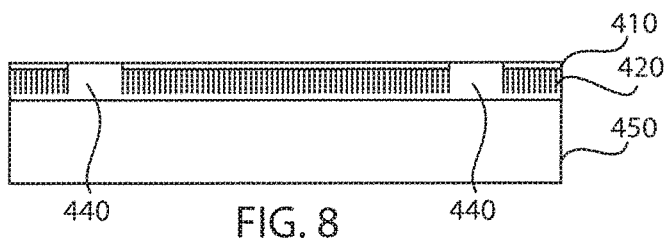
FIG. 8 is a cross-sectional view of the semiconductor device of FIG. 7 where a silicon (Si) substrate is removed, in accordance with an embodiment of the present invention.

FIG. 8 is a cross-sectional view of the semiconductor device of FIG. 7 where a silicon (Si) substrate is removed, in accordance with an embodiment of the present invention.

The structure of FIG. 7 is flipped and the substrate 405 is removed.

Figure 9:
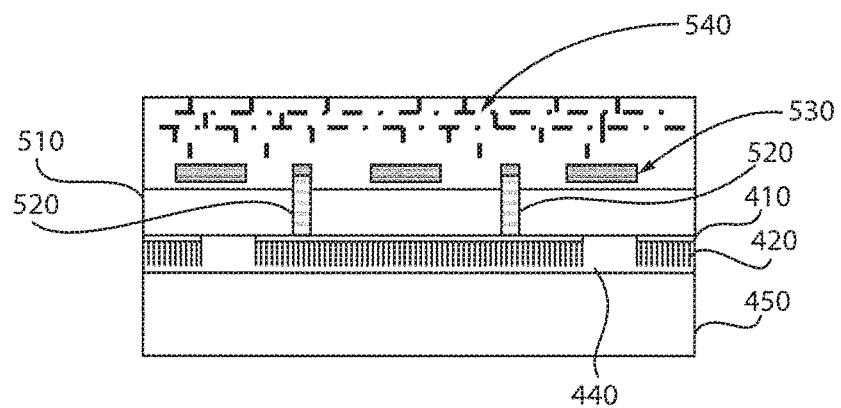
FIG. 9 is a cross-sectional view of the structure of FIG. 8 where carbon devices are built and wiring levels are added, in accordance with an embodiment of the present invention.

FIG. 9 is a cross-sectional view of the structure of FIG. 8 where carbon devices are built and wiring levels are added, in accordance with an embodiment of the present invention.

A polyimide (PI) layer 510 is formed over the carbon electrode structure of FIG. 8. Contacts or vias 520 are formed to the CNT or CNF layer 420. Carbon devices 530 are then built and wiring levels 540 are added.

Concerning PI layer 510, commercially available polyimide precursors (polyamic acid, acid-ester or ester) are various polyimide precursors from HD Microsystems (DuPont) and available under the trade designation Pyralin. These polyimide precursors come in many grades, including those available Pyralin polyimide precursors from HD Microsystems (DuPont) under the further trade designations PI-2555, PI-2545, PI-2560, PI-5878, PIH-61454, and PI-2540. Some of these are Pyromelletic Dianhydride-Oxydianiline (PMDA-ODA) polyimide precursors.

Commercially available chemically cured polyimides are various polyimides from HD Microsystems (DuPont) and available under the trade designation Kapton, including H-Hapton, V-Kapton, HN-Kapton, and VN-Kapton, which are all chemically cured polyimides. The chemically cured polyimides are generally cured with an anhydride curing agent such as acetic anhydride. Also, commercially available are Upilex polyimides from Ube Industries.

PI adhesive available from HD Microsystems under trade designation for experimental materials HD300x, where x indicates systematic number to identify different proprietary PI adhesive compositions and/or solids concentration, molecular weight, and viscosity of the solution tailored to particular application of the adhesive as determined by customer.

Concerning carbon devices 530, besides exhibiting intriguing quantum behaviors even at room temperature, carbon devices 530 exhibit at least two important characteristics, that is, a nanotube or nanofiber can be either metallic or semiconducting depending on its chirality, i.e., conformational geometry. Metallic carbon devices can carry an extremely large current density with constant resistivity. Semiconducting carbon devices can be electrically switched "on" or "off" as field effect transistors (FETs). The two types can be covalently joined (sharing electrons).

The carbon devices that can be used in the present invention are single walled or multi-walled nanomaterials that have an outer diameter that is typically from about 0.4 nm to about 30 nm, with an outer diameter from about 0.8 nm to about 3 nm being more typical, and a length that is typically from about 5 nm to about 100 µm, with a length from about 10 nm to about 10 µm being more typical. In addition to having an outer diameter, the carbon devices that can be used in the present invention have an inner diameter that is typically from about 0.4 nm to about 15 nm, with an inner diameter from about 0.8 nm to about 3 nm being more highly typical. The carbon devices useful in the present invention are further characterized as having a high aspect ratio that is typically on the order of about 5 or greater, with an aspect ratio from about 5 to about 10000 being more typical.

Carbon-based devices can first be produced using arc-discharge, laser ablation of a carbon target, or chemical vapor deposition, then suspended in solvents, and then assembled on the target substrate. Alternatively, carbon-based devices can also be made directly on the target substrate by chemical vapor deposition (CVD) in the presence of metallic particles on the target substrate. Along with the techniques illustrated above, the present invention also contemplates other techniques that are capable of forming nanostructures, such as carbon devices 530. For example, solution-phase decomposition, sol-gel electrophoresis, or wet-chemical, hydrothermal synthesis can be used in forming one-dimensional nanostructures.

Figure 10:
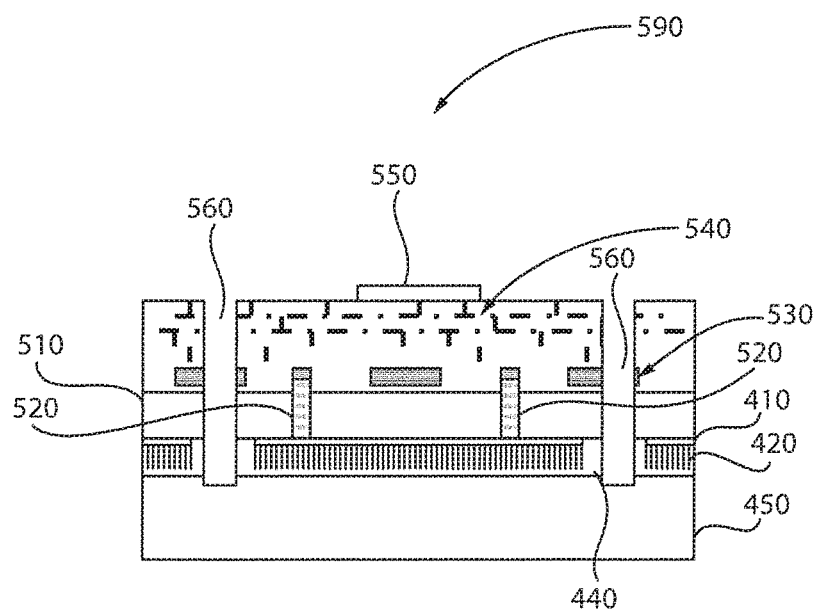
FIG. 10 is a cross-sectional view of the structure of FIG. 9 where a second bondpad and segmentation channels are formed, in accordance with an embodiment of the present invention.
Figure 11:
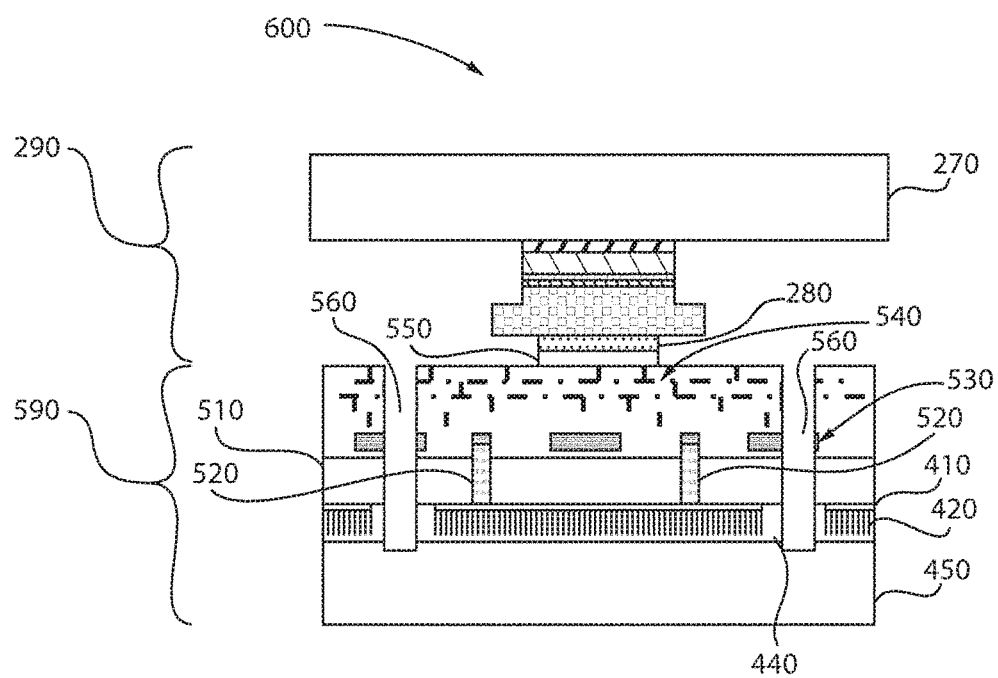
FIG. 11 is a cross-sectional view illustrating attachment of the LED structure of FIG. 5 to the carbon electrode sensor of FIG. 10 via the first and second bondpads, in accordance with an embodiment of the present invention.

FIG. 10 is a cross-sectional view of the structure of FIG. 9 where a second bondpad and segmentation channels are formed, in accordance with an embodiment of the present invention.

Segmentation channels 560 are formed and a bondpad 550 is also formed over the wiring levels 540. The structure of FIG. 10 is referred to as a carbon electrode sensor structure 590. The segmentation channels 560 extend through the wiring levels 540, through the carbon devices 530, through the PI layer 510, and through the PDMS layer 440 and partially into the handler 450. The segmentation channels 560 are aligned with the segmentation channels 425 (FIG. 6).

FIG. 11 is a cross-sectional view illustrating attachment of the LED structure of FIG. 5 to the carbon electrode sensor of FIG. 10 via the first and second bondpads, in accordance with an embodiment of the present invention.

The structure 290 of FIG. 5 is attached or bonded to the structure 590 of FIG. 10 such that the first bondpad 280 contacts or engages the second bondpad 550. The structure of FIG. 11 is referred to as a structure 600 where the LED and the sensor are combined or integrated or assembled.

Figure 12:
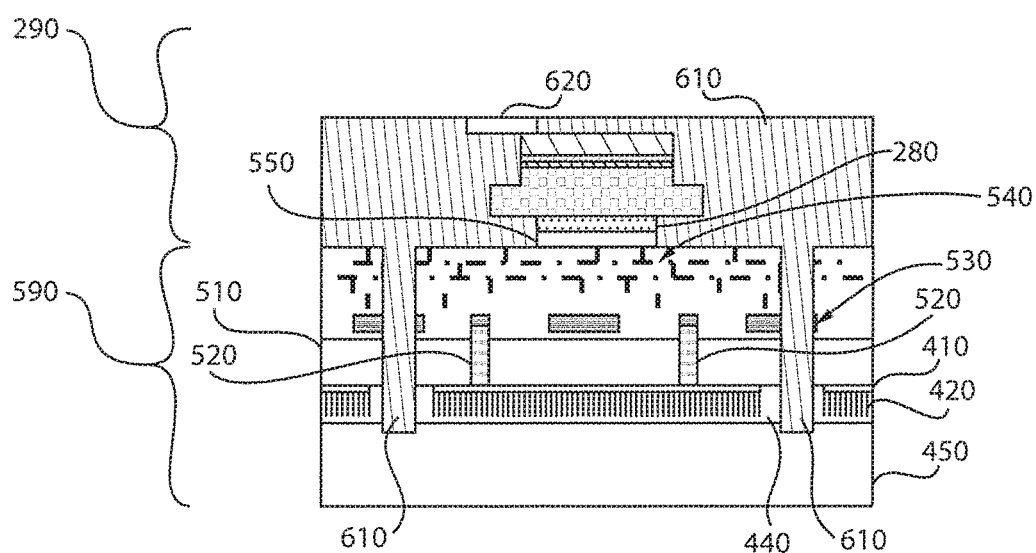
FIG. 12 is a cross-sectional view of the structure of FIG. 11 where the handler is released, an insulator is deposited, and an LED wire level is built, in accordance with an embodiment of the present invention.

FIG. 12 is a cross-sectional view of the structure of FIG. 11 where the handler is released, an insulator is deposited, and an LED wire level is built, in accordance with an embodiment of the present invention.

The glass handler 270 is removed and insulator 610 is deposited over the GaN layers. The insulator 610 is also received within the segmentation channels 560. Additionally, an LED wire level 620 is formed. The LED wiring can run in the z-plane.

The insulator 610 can be, e.g., a conformal oxide, nitride or oxynitride.

Figure 13:
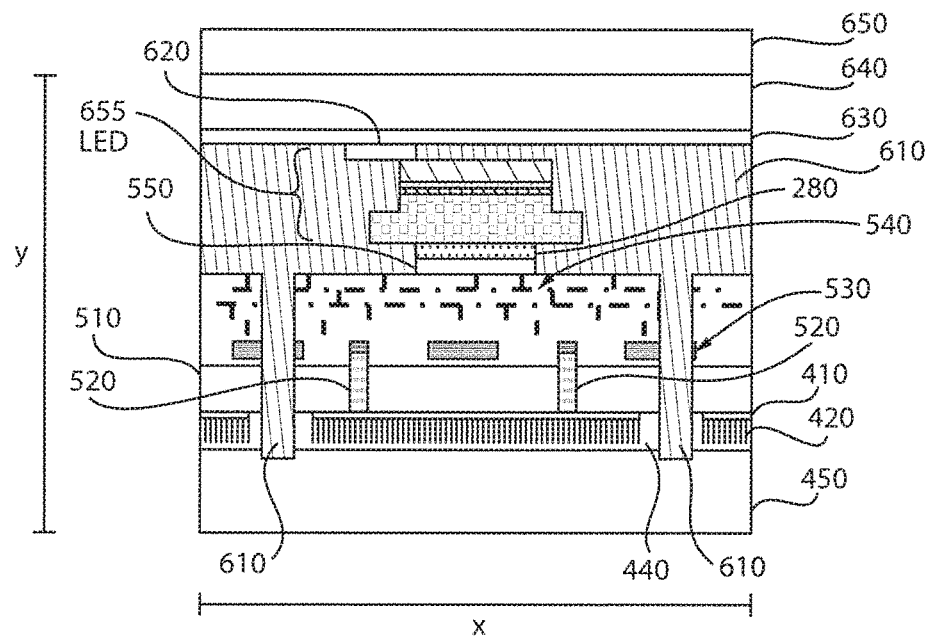
FIG. 13 is a cross-sectional view of the structure of FIG. 12 where a polyimide (PI) layer is deposited, a silicon nitride ($Si_3N_4$) layer is deposited, and a first dissolvable outer layer is applied, in accordance with an embodiment of the present invention.

FIG. 13 is a cross-sectional view of the structure of FIG. 12 where a polyimide (PI) layer is deposited, a silicon nitride ($Si_3N_4$) layer is deposited, and a first dissolvable outer layer is applied, in accordance with an embodiment of the present invention.

A PI layer 630 is formed over the structure of FIG. 12. A silicon nitride ($Si_3N_4$) layer 640 is then deposited over the PI layer 630. Subsequently, a first dissolvable outer layer 650 is applied over the $Si_3N_4$ layer 640. The structure can have a length "X" and a height "Y." The length can be, e.g., 50 µm and the height can be, e.g., 25 µm. One skilled in the art can contemplate various dimensions for such structure that are suitable for various intended application.

Figure 14:
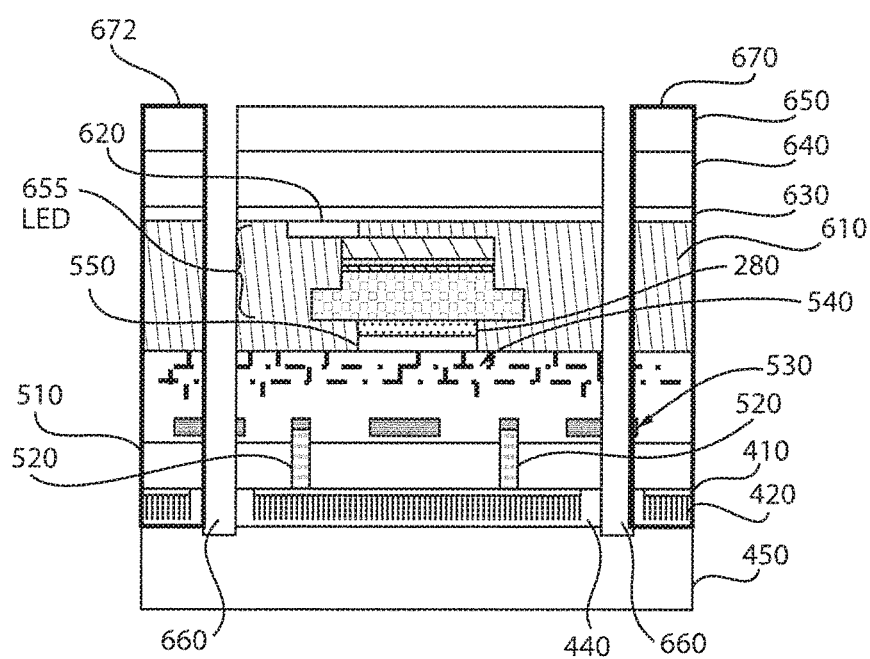
FIG. 14 is a cross-sectional view of the structure of FIG. 13 where segmentation channels are formed, in accordance with an embodiment of the present invention.

FIG. 14 is a cross-sectional view of the structure of FIG. 13 where segmentation channels are formed, in accordance with an embodiment of the present invention.

The segmentation channels 660 are formed such that a rightmost section 670 and a leftmost section 672 of the structure of FIG. 13 are separated from the LED 655. The segmentation channels 660 extend through the first dissolvable outer layer 650, through the $Si_3N_4$ layer 640, through the Pi layer 630, and through the insulator 610, such that the segmentation channels 660 are aligned with the segmentation channels 560 (FIG. 10). The segmentation channels 660 further extend through the wiring levels 540, through the carbon devices 530, through the PI layer 510, and through the PDMS layer 440 and partially into the handler 450.

Figure 15:
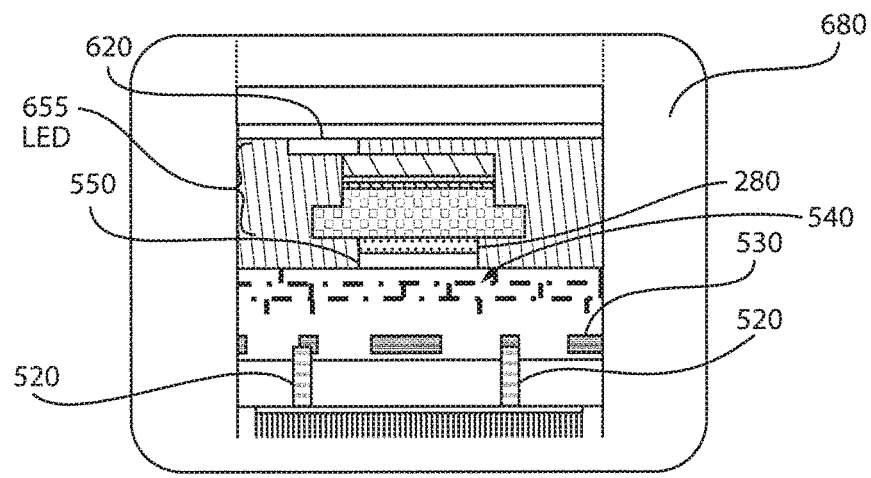
FIG. 15 is a cross-sectional view of the structure of FIG. 14 where a polydimethylsiloxane (PDMS) layer is removed and a second dissolvable layer is applied, in accordance with an embodiment of the present invention.

FIG. 15 is a cross-sectional view of the structure of FIG. 14 where a polydimethylsiloxane (PDMS) layer is removed and a second dissolvable layer is applied, in accordance with an embodiment of the present invention.

The handler 450 is removed, the PDMS layer 440 is removed, and the rightmost and leftmost sections 670, 672 are removed. Additionally, a second dissolvable outer layer 680 is applied. This is the final structure that can be embedded or integrated with the shank 120 of the probe 100 of FIG. 1. As noted above, a plurality of these structures can be incorporated into the shank 120 of the probe 100. It is further noted that the micro LED surface is in opposed relation to the carbon electrode sensors. The carbon electrode sensors are shown connected with silicon (Si) through vias to the carbon devices.

Figure 16:
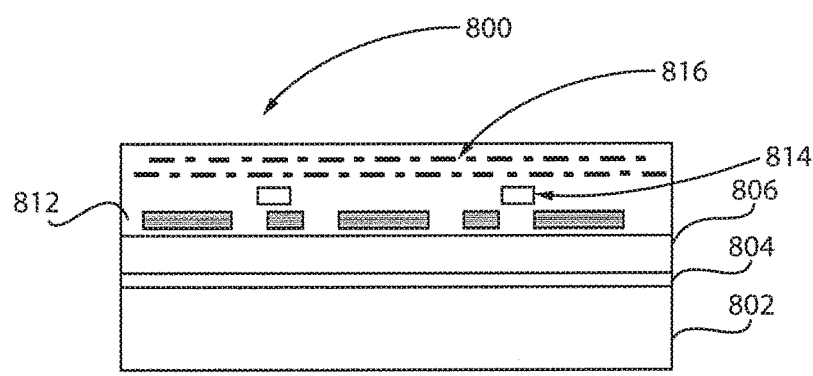
FIG. 16 is a cross-sectional view of a structure for a carbon nanotube horizontal sensor layer, in accordance with an embodiment of the present invention.

FIG. 16 is a cross-sectional view of a structure for a carbon nanotube horizontal sensor layer, in accordance with an embodiment of the present invention.

The structure 800 includes a PDMS layer 804 formed on a substrate 802. The substrate 802 can be, e.g., a Si substrate.

A PI layer 806 is formed over the PDMS layer 804. Subsequently, carbon devices 812, carbon electrodes 814, and wiring levels 816 are formed thereon.

Figure 17:
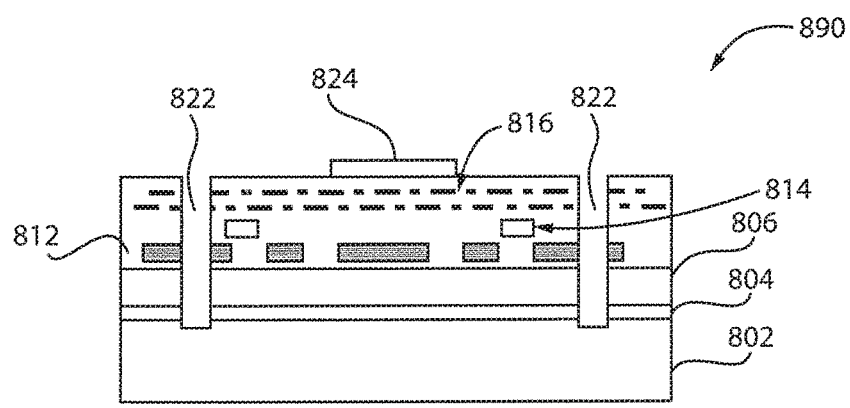
FIG. 17 is a cross-sectional view of FIG. 16 where a first bondpad and segmentations channels are formed, in accordance with an embodiment of the present invention.

FIG. 17 is a cross-sectional view of FIG. 16 where a first bondpad and segmentations channels are formed, in accordance with an embodiment of the present invention.

Segmentation channels 822 are formed, as well as a bondpad 824 is formed on the wiring levels 816. The segmentation channels 822 extend through the wiring levels 816, through the carbon devices 812, through the PI layer 806, and through the PDMS layer 804 and partially into the substrate 802. The structure of FIG. 17 is referred to as sensor structure 890. This is an alternative sensor structure compared to the sensor structure 590 of FIG. 10.

Figure 18:
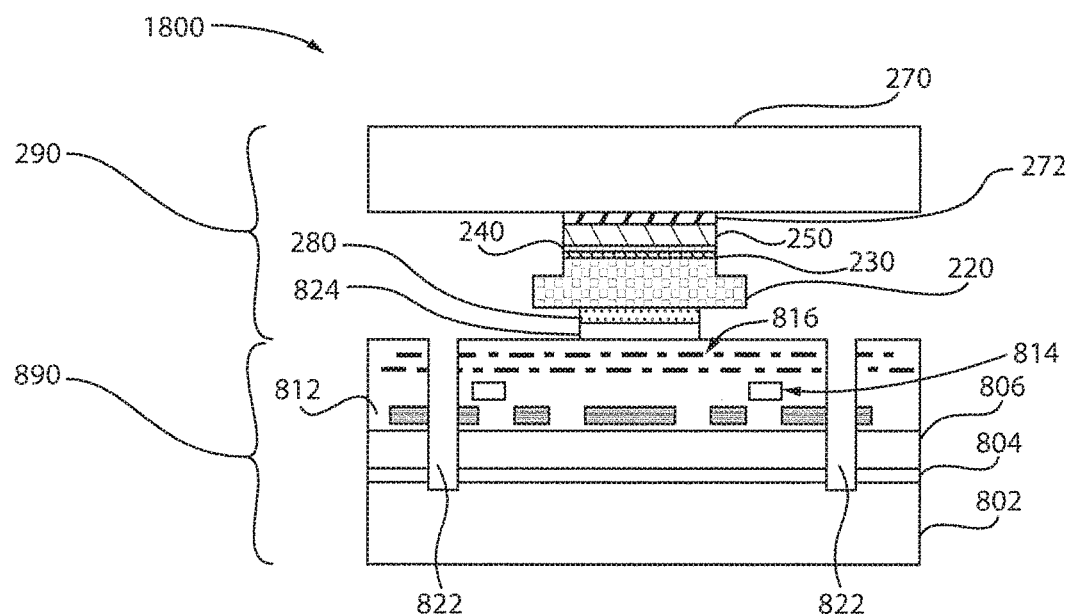
FIG. 18 is a cross-sectional view illustrating attachment of the LED structure of FIG. 5 to the sensor of FIG. 17 via the first and second bondpads, in accordance with an embodiment of the present invention.

FIG. 18 is a cross-sectional view illustrating attachment of the LED structure of FIG. 5 to the sensor of FIG. 17 via the first and second bondpads, in accordance with an embodiment of the present invention.

The structure 290 of FIG. 5 is attached or bonded to the structure 890 of FIG. 17 such that the first bondpad 280 contacts or engages the second bondpad 824. The structure of FIG. 18 is referred to as a structure 1800 where the LED and the sensor are combined or integrated or assembled to form a final structure.

Figure 19:
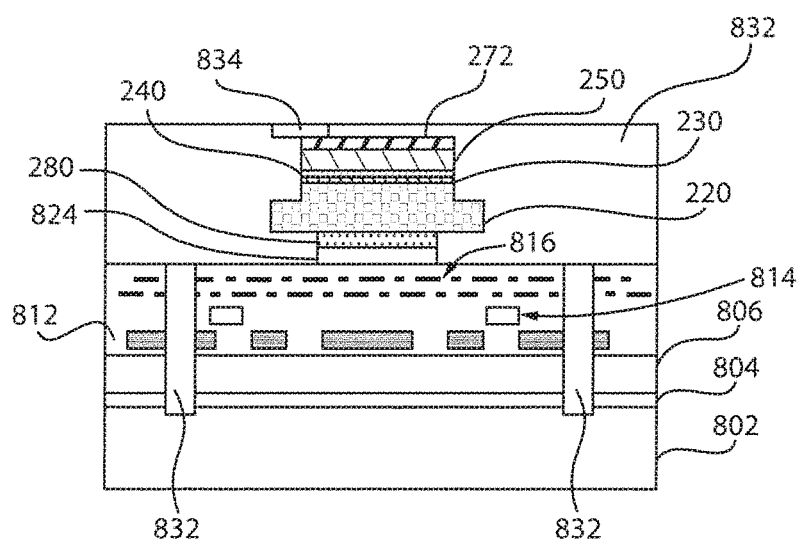
FIG. 19 is a cross-sectional view of the structure of FIG. 18 where the handler is released, an insulator is deposited, and an LED wire level is built, in accordance with an embodiment of the present invention.

FIG. 19 is a cross-sectional view of the structure of FIG. 18 where the handler is released, an insulator is deposited, and an LED wire level is built, in accordance with an embodiment of the present invention.

The glass handler 270 is removed and insulator 832 is deposited over the GaN layers. The insulator 832 is also received within the segmentation channels 822. Additionally, an LED wire level 834 is formed. The LED wiring can run in the z-plane.

Figure 20:
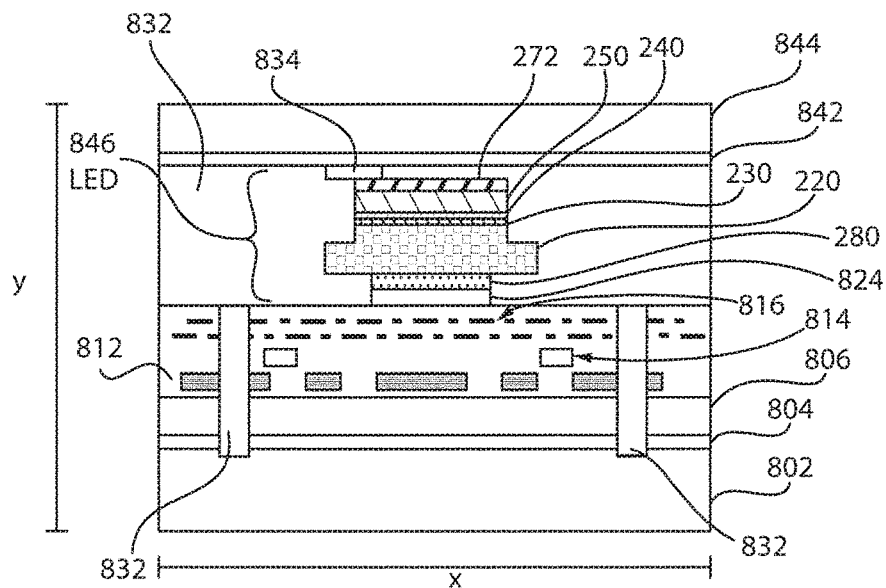
FIG. 20 is a cross-sectional view of the structure of FIG. 19 where a polyimide (PI) layer and a silicon nitride ($Si_3N_4$) layer are deposited, in accordance with an embodiment of the present invention.

FIG. 20 is a cross-sectional view of the structure of FIG. 19 where a polyimide (PI) layer and a silicon nitride ($Si_3N_4$) layer are deposited, in accordance with an embodiment of the present invention.

A silicon nitride ($Si_3N_4$) layer 842 is formed over the structure of FIG. 19. A PI layer 844 is then deposited over the $Si_3N_4$ layer 842. The structure can have a length "X" and a height "Y." The length can be, e.g., 50 µm and the height can be, e.g., 25 µm. One skilled in the art can contemplate various dimensions for such structure that are suitable for various intended application.

Figure 21:
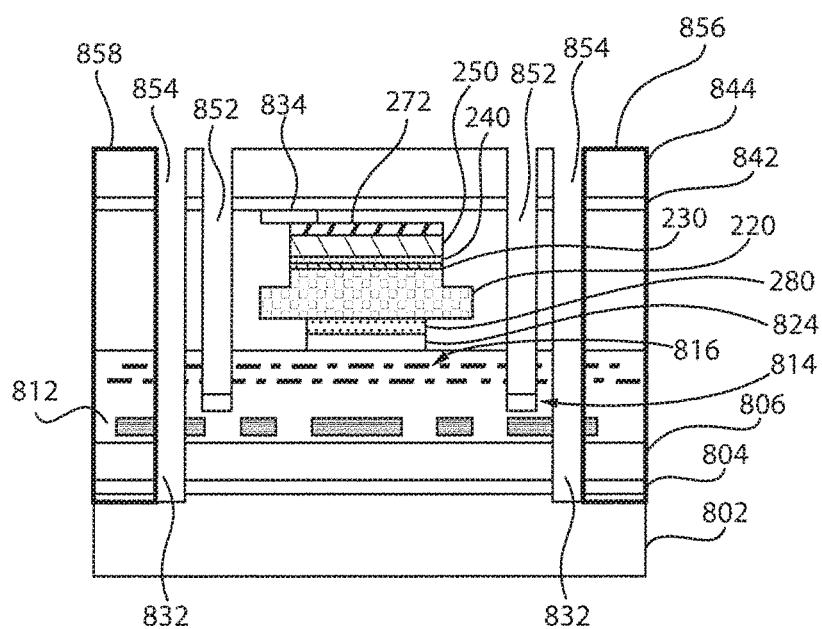
FIG. 21 is a cross-sectional view of the structure of FIG. 20 where segmentation channels are formed, in accordance with an embodiment of the present invention.

FIG. 21 is a cross-sectional view of the structure of FIG. 20 where segmentation channels are formed, in accordance with an embodiment of the present invention.

The segmentation channels 854 are formed such that a rightmost section 856 and a leftmost section 858 of the structure of FIG. 20 are separated from the LED 846. The segmentation channels 854 extend through the PI layer 844, through the $Si_3N_4$ layer 842, and through the insulator 832, such that the segmentation channels 854 are aligned with the segmentation channels 822 (FIG. 18). The segmentation channels 854 further extend through the wiring levels 816, through the carbon devices 812, through the PI layer 806, and through the PDMS layer 804 and partially into the substrate 802.

Figure 22:
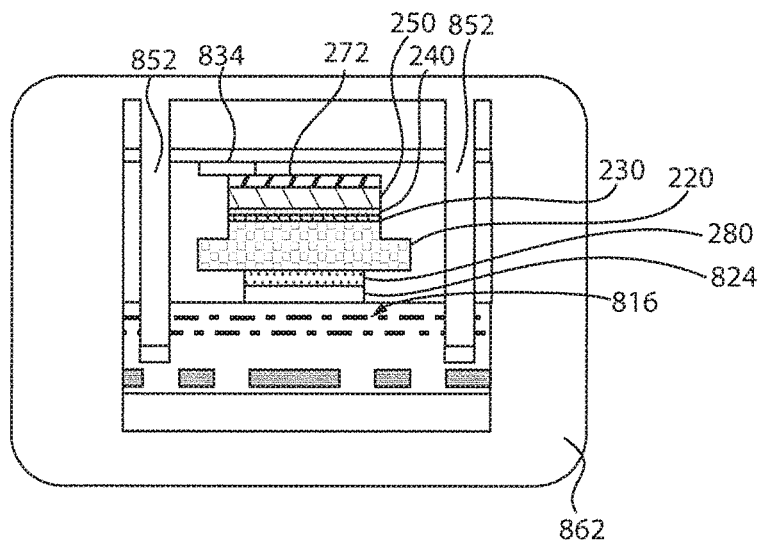
FIG. 22 is a cross-sectional view of the structure of FIG. 21 where first and second dissolvable layers are applied, in accordance with an embodiment of the present invention.

FIG. 22 is a cross-sectional view of the structure of FIG. 21 where first and second dissolvable layers are applied, in accordance with an embodiment of the present invention.

The substrate 802 is removed, and first and second dissolvable outer layer, 862 are applied. This is the final structure that can be embedded or integrated with the shank 120 of the probe 100 of FIG. 1. As noted above, a plurality of these structures can be incorporated into the shank 120 of the probe 100. Moreover, it is contemplated that the shank 120 of the probe 100 of FIG. 1 can be configured to accommodate both the structures shown in FIGS. 15 and 22. It is contemplated that such structures can be selectively activated. In other words, in one example, a user of the probe 100 can have the capability to activate/deactivate various portions or types of the LEDs. In this example embodiment, the micro LEDs face the same direction as the carbon electrode sensors. The carbon electrode sensors are, e.g., horizontally aligned carbon nanotubes (CNT).

Figure 23:
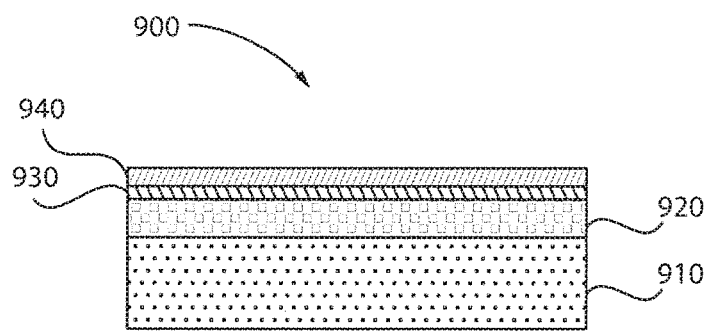
FIG. 23 is a cross-sectional view of an LED die on a blanket film gallium nitride (GaN) wafer, in accordance with an embodiment of the present invention.

FIG. 23 is a cross-sectional view 900 of an LED die on a blanket film gallium nitride (GaN) wafer, in accordance with an embodiment of the present invention.

GaN buffer layers are formed on a sapphire substrate 910. The sapphire substrate 910 can be formed of, e.g., $Al_2O_3$ (aluminum oxide). The GaN buffer layers include a first layer 920, a second layer 930, and a third layer 940. The first layer 920 can be, e.g., n-type GaN. The second layer 930 can be, e.g., GaInN. The third layer 940 can be, e.g., p-type GaN.

The p-type GaN layer 940 is in a contrast to the n-type GaN layer 920. Namely, electrons are drifted by an external voltage in the n-type GaN layer 920, while holes are drifted by the external voltage in the p-type GaN layer 940. Therefore, the holes and the electrons are mutually recombined to thereby emit light. The p-type GaN layer 940 can have a thickness of about 0.2 µm. The n-type GaN layer 920 can have a thickness of about 2.5 µm. The GaInN layer 930 can have a thickness of about 0.2 µm.

Figure 24:
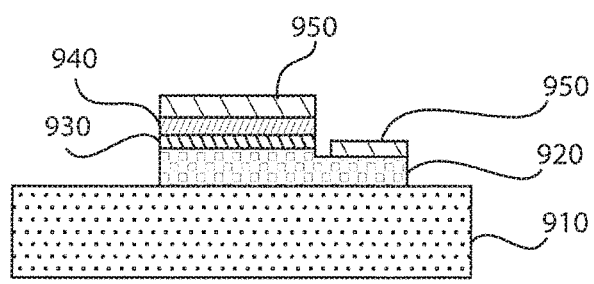
FIG. 24 is a cross-sectional view of the structure of FIG. 23 where the GaN layers are selectivity etched such that two GaN contacts are formed, in accordance with an embodiment of the present invention.

FIG. 24 is a cross-sectional view of the structure of FIG. 23 where the GaN layers are selectivity etched such that two GaN contacts are formed, in accordance with an embodiment of the present invention.

The GaN layers 920, 930, 940 are etched to form two contacts 950 on different portions of the GaN layers. The first contact 950 is formed over the first layer 920 (i.e., n-type GaN), whereas the second contact 950 is formed over the third layer 940 (i.e., p-type GaN). The two contacts 950 are separate and distinct from each other.

The metal contacts 950 include any metal or metal-like element that can react with carbon to form a stable binary metal carbide. Alternatively, the metal can include C and optionally other elements. Examples of such metals include: Al, Si, Sc, Ti, V, Cr, Mn, Fe, Y, Zr, Nb, Mo, Hf, Ta, W and mixtures or alloys thereof. In a preferred embodiment, at least one of Al, Ti, Cr, Mo, W, Zr, Hf or Ta is used as the metal contact 950. The compound formation can be performed in different atmospheres such as, for example, nitrogen, forming gas, chloride, bromide, fluoride, oxygen and others. The variation of ambient gases allows for the formation of different conductive compounds. The metal contact 950 can be formed in the present invention utilizing a conformal deposition process, such as, for example, CVD, PECVD, chemical solution deposition, ALD, sputtering, plating, evaporation or other like processes. The thickness of the metal contact 950 can vary depending on the metal used as well as the technique that was used to form the same. Typically, the thickness of the metal contact 950 can be from about 3 to about 200 nm, with a thickness from about 5 to about 50 nm being more typical.

Figure 25:
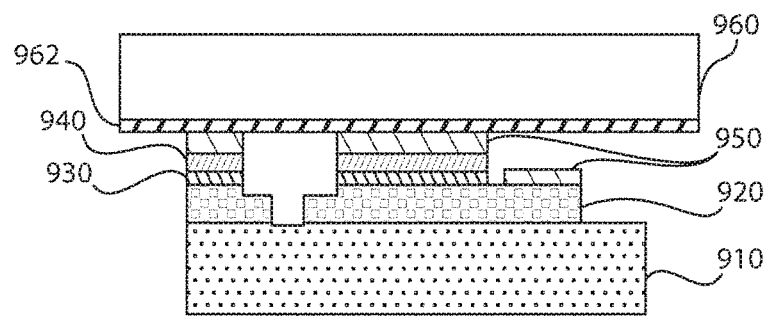
FIG. 25 is a cross-sectional view of the structure of FIG. 24 where the structure is transferred to a handler, in accordance with an embodiment of the present invention.

FIG. 25 is a cross-sectional view of the structure of FIG. 24 where the structure is transferred to a handler, in accordance with an embodiment of the present invention.

The structure is transferred to a first handler 960. The first handler 960 can be, e.g., a glass handler. A release layer 962 can be applied to the first handler 960.

Figure 26:
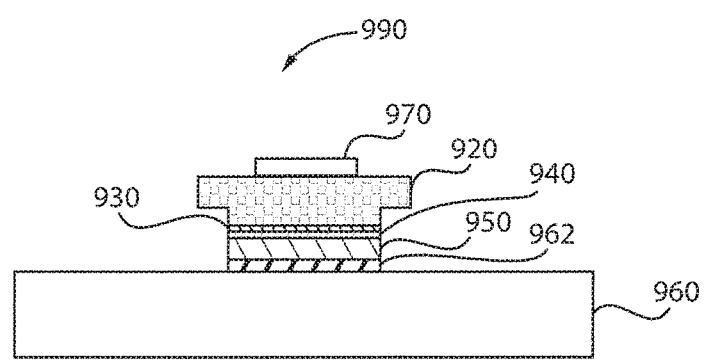
FIG. 26 is a cross-sectional view of the semiconductor device of FIG. 25 where a sapphire substrate is removed and a first bondpad is formed over a GaN layer, in accordance with an embodiment of the present invention.

FIG. 26 is a cross-sectional view of the semiconductor device of FIG. 25 where a sapphire substrate is removed and a first bondpad is formed over a GaN layer, in accordance with an embodiment of the present invention.

The sapphire substrate 910 (FIG. 25) is released or removed and a first bondpad 970 is formed on the layer 920. The structure of FIG. 26 is referred to as LED structure 990.

Figure 27:
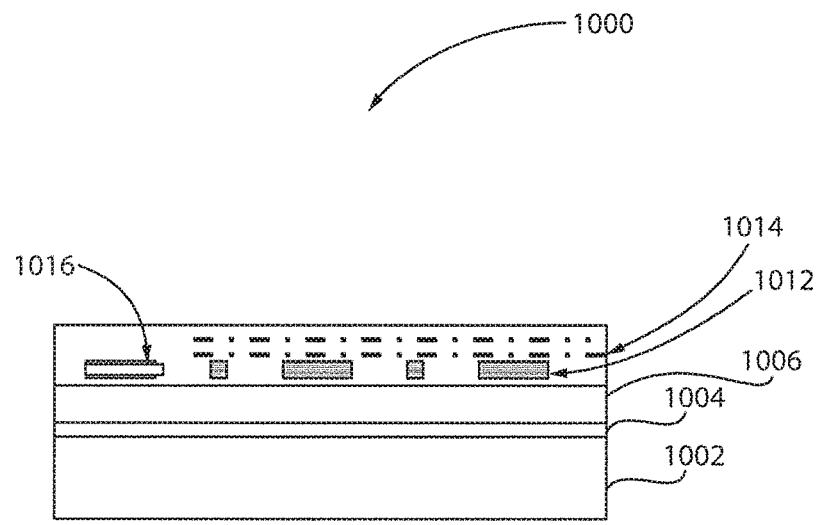
FIG. 27 is a cross-sectional view of a carbon nanotube horizontal structure for a sensor, in accordance with an embodiment of the present invention.

FIG. 27 is a cross-sectional view of a carbon nanotube horizontal structure for a sensor, in accordance with an embodiment of the present invention.

Figure 28:
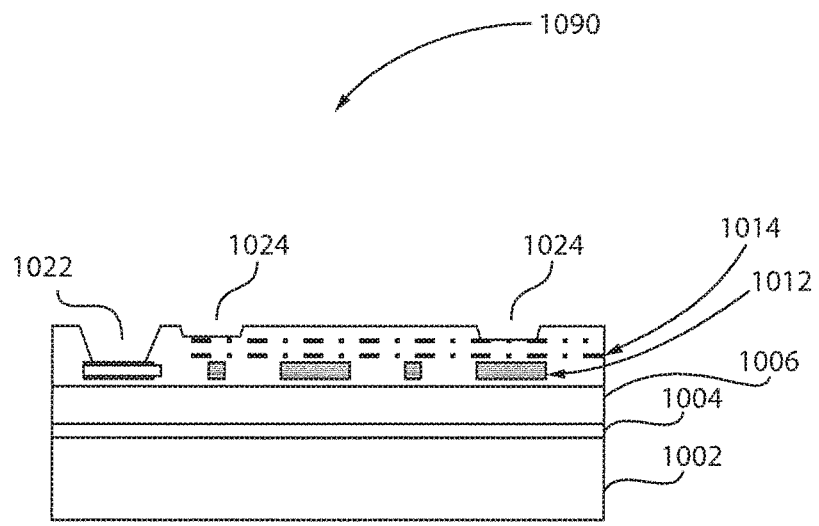
FIG. 28 is a cross-sectional of the structure of FIG. 27 where vias are formed, in accordance with an embodiment of the present invention.
Figure 29:
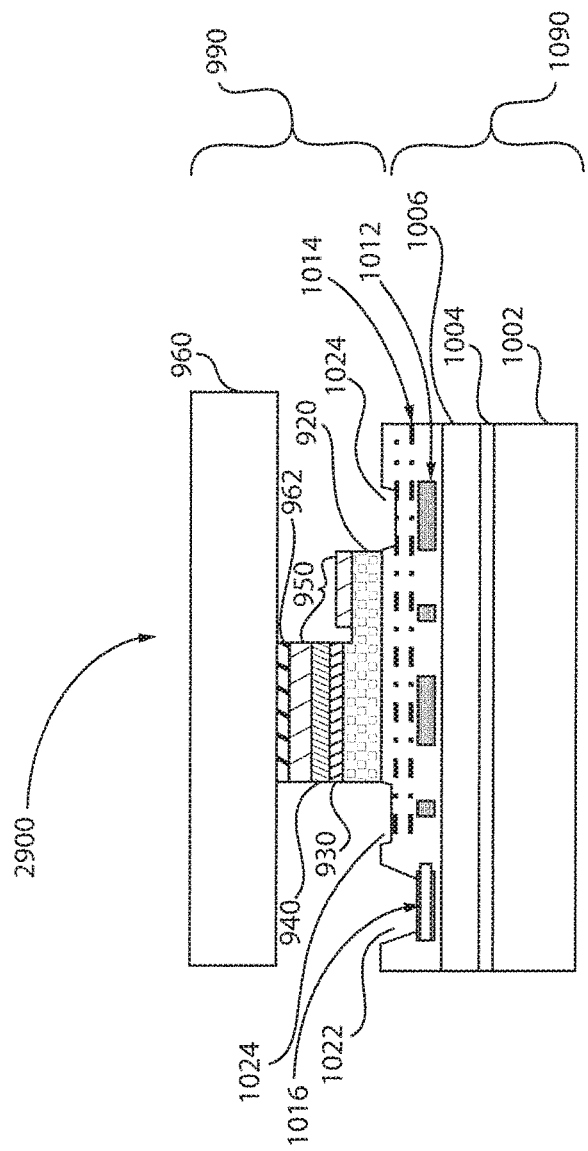
FIG. 29 is a cross-sectional view illustrating attachment of the LED structure of FIG. 26 to the carbon electrode sensor of FIG. 28 via the first and second bondpads, in accordance with an embodiment of the present invention.

After forming the LED structure 990, as described above with reference to FIGS. 23-26, the sensor portion is now formed with reference to FIGS. 27-28. The LED structure 990 will be combined with the sensor portion to form the final structure (FIG. 29).

The structure 1000 includes a PDMS layer 1004 formed on a substrate 1002. The substrate 1002 can be, e.g., a Si substrate. A PI layer 1006 is formed over the PDMS layer 1004. Subsequently, carbon devices 1012, carbon electrodes 1014, and wiring levels 1016 are formed thereon.

FIG. 28 is a cross-sectional of the structure of FIG. 27 where vias are formed, in accordance with an embodiment of the present invention.

Vias 1022 and 1024 are formed. The vias 1024 extend through a portion of the wiring levels 1016, whereas the via 1022 extends through the wiring levels 1016 and up to the carbon electrodes 1014 and/or the carbon devices 1012. The structure of FIG. 28 is referred to as sensor structure 1090.

FIG. 29 is a cross-sectional view illustrating attachment of the LED structure of FIG. 26 to the carbon electrode sensor of FIG. 28 via the first and second bondpads, in accordance with an embodiment of the present invention.

The structure 990 of FIG. 26 is attached or bonded or integrated with the structure 1090 of FIG. 28 such that the first layer 920 contacts or engages the wiring levels 1016 such that the first layer 920 is positioned between the vias 1024. The structure of FIG. 29 is referred to as a structure 2900 where the LED and the sensor are combined.

Therefore, in summary, the neural probe of the present invention allows for stimulation at the electrode-tissue interface and for recording the neural response and the resulting neurochemical release of dopamine, serotonin, adenosine, DOPAC at the same time (sequentially). The neural probe can be a flexible neural probe structure with optogenetic μLEDS, carbon electronics, and carbon electrode sensors. Stated differently, the neural probe can be a fully flexible carbon-based implantable electrode probe for multi-functional dopamine and pH sensing with local optogenetic neural activation achieved by combining or integrating or bonding the μLED structures with the carbon electrode sensors described herein.

It is to be understood that the present invention will be described in terms of a given illustrative architecture; however, other architectures, structures, substrate materials and process features and steps/blocks can be varied within the scope of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical mechanisms (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present embodiments. The compounds with additional elements will be referred to herein as alloys.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C)

only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Having described preferred embodiments of a method of device fabrication and a semiconductor device thereby fabricated for reducing parasitic back gate capacitance (which are intended to be illustrative and not limiting), it is noted that modifications and variations can be made by persons skilled in the art in light of the above teachings. It is therefore to be understood that changes can be made in the particular embodiments described which are within the scope of the invention as outlined by the appended claims. Having thus described aspects of the invention, with the details and particularity required by the patent laws, what is claimed and desired protected by Letters Patent is set forth in the appended claims.

What is claimed is:

1. A flexible neural probe comprising:
a probe body;
a shank extending from the probe body to a tip;
a plurality of micro light-emitting diodes (LEDs) extending sequentially along an entire length of a first surface of the shank for providing neuron-affecting light; and
a plurality of electrode sensor structures positioned across a length of a second surface of the shank, wherein each of the plurality of electrode sensor structures is integrated with a respective micro-LED of the plurality of micro LEDs to form single unitary components each defining a stacked configuration;
wherein each of the plurality of electrode sensor structures includes a carbon nanotube or carbon nanofiber layer, carbon devices, and wiring levels such that vias extend from the electrode devices to the carbon nanotube or carbon nanofiber layer; and
wherein the plurality of micro LEDs optogenetically activate neurons and the plurality of electrode sensor structures electrochemically record neurotransmitters and resulting neurochemistry, simultaneously, as neuronal data is being collected.

2. The neural probe of claim 1, wherein the wiring levels extend a horizontal length of each of the plurality of electrode sensor structures.

3. The neural probe of claim 1, wherein the carbon devices are positioned directly between the carbon nanotube or carbon nanofiber layer and the wiring levels.

4. The neural probe of claim 1, wherein each of the plurality of micro LEDs are defined on an LED die on a blanket film wafer.

5. The neural probe of claim 4, wherein the LED die is transferred to a first handler, a sapphire substrate of the wafer is removed, and a first bondpad is formed on an exposed semiconductor layer.

6. The neural probe of claim 5, wherein each of the plurality of electrode sensor structures is formed by patterning segmentation channels.

7. The neural probe of claim 6, wherein a release layer is applied and a second handler is bonded to each of the plurality of electrode sensor structures.

8. The neural probe of claim 7, wherein a polyimide (PI) layer is disposed directly between the carbon nanotube or carbon nanofiber layer and the carbon devices.

9. The neural probe of claim 1, wherein each respective micro LED is attached to each respective electrode sensor structure via first and second bondpads.

10. The neural probe of claim 1, wherein a portion of the carbon devices of an electrode structure are vertically misaligned with respect to a respective micro LED.

11. A flexible neural probe comprising:
a probe body;
a shank extending from the probe body to a tip;
a plurality of micro light-emitting diodes (LEDs) extending sequentially along an entire length of a first surface of the shank for providing neuron-affecting light; and
a plurality of electrode sensor structures positioned across a length of a second surface of the shank, wherein each of the plurality of electrode sensor structures is integrated with a respective micro-LED of the plurality of micro LEDs to form single unitary components each defining a stacked configuration;
wherein each of the plurality of electrode sensor structures includes a carbon nanotube or carbon nanofiber layer, carbon devices, and wiring levels such that vias extend from the electrode devices to the carbon nanotube or carbon nanofiber layer; and
wherein the plurality of micro LEDs optogenetically activate neurons and the plurality of electrode sensor structures electrochemically record neurotransmitters and resulting neurochemistry, simultaneously, as neuronal data is being collected.

12. The neural probe of claim 11, wherein each of the plurality of micro LEDs are defined on an LED die on a blanket film wafer.

13. The neural probe of claim 12, wherein the LED die is transferred to a first handler, a sapphire substrate of the wafer is removed, and a first bondpad is formed on an exposed semiconductor layer.

14. The neural probe of claim 13, wherein each of the plurality of electrode sensor structures is formed by patterning segmentation channels.

15. The neural probe of claim 14, wherein a release layer is applied and a second handler is bonded to each of the plurality of electrode sensor structures.

16. The neural probe of claim 15, wherein a polyimide (PI) layer is disposed directly between the carbon nanotube or carbon nanofiber layer and the carbon devices.

17. The neural probe of claim 16, wherein each respective micro LED is attached to each respective electrode sensor structure via first and second bondpads.

18. The neural probe of claim 11, wherein a portion of the carbon devices of an electrode structure are vertically misaligned with respect to a respective micro LED.

19. The neural probe of claim 11, wherein the carbon devices are positioned directly between the carbon nanotube or carbon nanofiber layer and the wiring levels.

20. A method of stimulating excitable tissue, the method comprising:
   introducing a flexible neural probe into target excitable tissue, the neural probe including:
   a probe body;
   a shank extending from the probe body to a tip;
   a plurality of micro light-emitting diodes (LEDs) extending sequentially along an entire length of a first surface of the shank for providing neuron-affecting light; and
   a plurality of electrode sensor structures positioned across a length of a second surface of the shank, wherein each of the plurality of electrode sensor structures is integrated with a respective micro-LED of the plurality of micro LEDs to form single unitary components each defining a stacked configuration;
   wherein each of the plurality of electrode sensor structures includes a carbon nanotube or carbon nanofiber layer, carbon devices, and wiring levels such that vias extend from the electrode devices to the carbon nanotube or carbon nanofiber layer; and
   optogenetically activating neurons via the plurality of micro LEDs and electrochemically recording neurotransmitters and resulting neurochemistry via the plurality of electrode sensor structures, simultaneously, as neuronal data is being collected.

* * * * *